United States Patent [19]

Kool et al.

[11] Patent Number: 5,107,024

[45] Date of Patent: Apr. 21, 1992

[54] DIPHENYLAMINE PURIFICATION

[75] Inventors: Pieter Kool, Oostvoorne, Netherlands; Eliezer L. Sigall, Paris; Samuel Meghir, Port Marly, both of France

[73] Assignee: Atochem Agri, S.A., Plaisir, France

[21] Appl. No.: 703,958

[22] Filed: May 22, 1991

Related U.S. Application Data

[63] Continuation-in-part of Ser. No. 499,854, Mar. 27, 1990, abandoned.

[51] Int. Cl.$^5$ .............................................. C07C 209/84
[52] U.S. Cl. ...................................... 564/433; 564/437
[58] Field of Search ................................ 564/433, 437

[56] References Cited

U.S. PATENT DOCUMENTS 2,256,196  9/1941  Filbert ................................. 564/433
4,667,048  5/1987  Inoue et al. ........................ 556/469

FOREIGN PATENT DOCUMENTS 0102544   8/1980   Japan ................................. 564/433
0270930   5/1927   United Kingdom ................ 564/437
0910130  11/1962   United Kingdom ................ 564/433

OTHER PUBLICATIONS

Majewski, T. et al., "Separation of Diphenylamine & Azobenzene," CA, vol. 69, No. 10192c (1968).
Velea, I. et al., "Purification of Diphenylamine," CA, vol. 78, No. 147537z (1973).

*Primary Examiner*—Richard L. Raymond

[57] ABSTRACT

Selective removal of primary amines from technical grade diphenylamine by contacting a solvent solution of said diphenylamine with a cationic exchange resin having sulfonic acid group functionality in the presence of up to about 3 percent water.

3 Claims, No Drawings

DIPHENYLAMINE PURIFICATION

CROSS-REFERENCE TO RELATED APPLICATION

This application is a continuation-in-part of application Ser. No. 499,854, filed Mar. 27, 1990, now abandoned.

FIELD OF THE INVENTION

This invention relates to purification of the secondary amine, diphenylamine ("DPA"), by means of ion exchange and to the resulting purified product. More particularly, it relates to the purification of technical grade DPA (including formulations containing technical grade DPA) contaminated with various by-products, especially primary amines such as aniline, 4-aminobiphenyl ("4-ABP") and 2-aminobiphenyl ("2-ABP").

BACKGROUND OF THE INVENTION

DPA is widely used in post-harvest treatments as an anti-oxidant to protect fruit such as apples and pears during long cold-storage against the physiological disease, scald. DPA also has fungicidal activity. It is often formulated as an emulsifiable concentrate which, after dilution with water, can be used as such or in combination with waxes by dipping the fruit into the liquid to cover it with a protective layer.

"Technical grade" DPA available commercially contains a number of by-products (such as acridine, aniline, quinoline, indole, 4-ABP, and 2-ABP) which are inherent to the manufacturing process. Processes for manufacturing DPA are taught in the literature; for example, Kirk-Othmer's Encyclopedia of Chemical Technology gives an overview of such processes in the section describing manufacture of aromatic diarylamines. Several of the aforementioned by-products are of toxicological concern, especially 4-ABP which is a recognized carcinogenic compound. Aniline and 2-ABP are also suspected in this respect. It is therefore important to remove these impurities to a level as low as possible to reduce the risk of human health when consuming fruits thus treated with DPA.

While purification of technical grade DPA can be achieved by well-known techniques such as distillation or re-crystallization, these methods involve high energy costs for heating and cooling. It is an aim of this invention to find a more efficient method for selective removal of the impurities of toxicological concern. Guidelines for these impurities are under review by the World Health Organization, but it is expected that guideline impurity limits will be set at a maximum of 0.5 milligrams/kilogram ("mg/kg") for 4-ABP and a maximum of 2 mg/kg for each of 2-ABP and aniline. Thus, a further aim of this invention is to find a method for preparing a purified, food grade quality, DPA whose level of aniline, 2-ABP and 4-ABP are well below the guideline limits.

Applicants are not aware of any literature disclosing the use of ion exchange resins to achieve DPA purification.

SUMMARY OF THE INVENTION

A process is provided for selectively removing primary amines from DPA wherein (1) a solution containing DPA and an organic solvent is brought into contact with a cationic exchange resin having a sulfonic acid group functionality in the presence of up to about 3 percent water, based on the weight of the solution, and (2) the resulting, purified solution is then separated from the resin. This can be done either in a continuous process by passing the DPA solution over a column containing the resin or in a batch process by stirring the DPA solution with the resin, and afterwards removing the resin by decanting or filtering. The continuous process is preferred. Preferred solvents include ethanol or acetone.

It is advantageous when making an emulsifiable concentrate of DPA to use as the starting solution for the purification process an emulsifiable concentrate of technical grade DPA.

DETAILED DESCRIPTION OF THE INVENTION

It has now been found that the primary amines of toxicological concern (aniline, 2-ABP, and 4-ABP) can be removed from technical grade DPA to food grade purity by bringing a solution of technical grade DPA in an organic solvent into contact with resin-type strong acid cation exchangers, continuously or batchwise as aforesaid, in the presence of from 0 to about 3.0 weight percent water, based on the weight of the solution.

In one embodiment the starting solution is comprised of technical grade DPA and the organic solvent. In this embodiment, the purified DPA solution can be processed in any of several ways. Thus, solvent can be removed for possible re-use by distillation and the obtained DPA can be formulated, for instance, as an emulsifiable concentrate; or the purified DPA solution can be cooled until part of the DPA crystallizes and, after filtration, the obtained DPA can be formulated and the filtrate saved for re-use; or the purified DPA solution can be used as such in preparation of a formulation. Preferred solvents for this embodiment are those which have a good solubility for the DPA and are of a polar nature to afford reaction between the impurities and the resin. Examples are acetone, methyl ethyl ketone, methanol, ethanol, isopropanol, dimethylformamide, acetonitrile, ethylformiate, (poly)alkylene glycol ethers and esters thereof, alkylphenylpoly(alkyleneglycol)ethers, or mixtures thereof. Final choice of the solvent may be dictated by the manner chosen for processing of the purified DPA solution. The amount of solvent used varies greatly depending on the nature of the solvent. With such polar solvents, little or no water is required to be present. However, when apolar solvents are used, such as paraffin oil (white mineral oil, consisting of a mixture of branched alkanes) or other hydrocarbon oils, the purification is usually carried out in the presence of up to 3.0 weight percent water, preferably 1.0 to 2.0%, most preferably 1.5%. The water can be added to the solution, but it is preferred to add it to the resin since this results in more efficient activation of the resin.

In a second embodiment, where the starting solution is an emulsifiable concentrate of the technical grade DPA, it is preferred to use the apolar solvents in the presence of water, as aforesaid. Such concentrates also typically contain emulsifiers such as polyethylene glycol esters, ethoxylated fatty acids or alcohols, and ethoxylated alkyl aryl phenols, and, usually, an antifoam agent. In the formulation, the emulsifiers or detergents act as co-solvents. In this embodiment the resin can be separated from the purified concentrate by decantation and filtration or, preferably, by means of a D-Canter (centrifuge).

The cationic exchange resin is preferably a sulfonated poly(styrene divinylbenzene) copolymer resin of 10–500 mesh (preferably 20–50 mesh) with a rate of crosslinking between 1 and 30 (preferably 20–25%). Such resins are available commercially. The resin should have the sulfonic acid group in its acidic form or should be transformed into this form (if in its salt form) before use by treating the resin with, for example, a hydrochloric acid solution.

Temperatures are not critical and will normally be kept in a range of from about 15° C. to 50° C. It is desirable to avoid very low temperatures as they increase viscosity and decrease DPA solubility in the solvent and the absorption rate of the impurities by the resin. Very high temperatures lead to darkening of the DPA solution in some cases.

Contact times or flow-rates are dependent variables which vary with temperature, solvent, type and amount of resin, level of impurities in the technical DPA, and so on. Analysis of samples can be done during the process, such as by high performance liquid chromatography ("HPLC"), to indicate when removal of impurities to the desired level has been achieved.

EXAMPLE 1 - BATCH PROCESS WITH ACETONE

In a 150 ml flask provided with a stirrer and a reflux condensor was placed 25 grams ("g") of technical grade DPA (impurities given below in Table 1) and 50 milliliters ("ml") of acetone. The flask was placed in a 40° C. water-bath and the contents stirred until all DPA dissolved. Then added as the cationic exchange resin was a 20–50 mesh sulfonated poly(styrene divinylbenzene) copolymer resin having the sulfonic acid group in its acidic form and stirring at 40° C. was continued for 5.5 hours. The resin was removed from the DPA solution by filtration and purified DPA was isolated by evaporation. Recovered were 23.5g of DPA (94% yield). HPLC analysis of the starting material and the purified product for aniline, 2-ABP, and 4-ABP showed:

TABLE 1

|  | Aniline | 2-ABP | 4-ABP |
| --- | --- | --- | --- |
| Starting Material | 1.45 mg/kg | 22.29 mg/kg | 6.77 mg/kg |
| Purified Material | 0.08 mg/kg | 0.56 mg/kg | <0.01 mg/kg |
| % Removed | 95 | 97 | >99 |

EXAMPLE 2 - BATCH PROCESS WITH ETHANOL

In a 2 liter flask provided with a stirrer was placed 250g technical DPA and 1000 ml of ethanol (95%). The mixture wa stirred at 20° C. until all DPA had dissolved and then was added the same resin as in Example 1. Stirring was continued for 6 hours after which the clear solution was separated from the resin by decantation. From the solution the ethanol was removed by distillation from a rotating evaporator. Obtained was 242g purified DPA (97% yield). Analysis by HPLC gave the following results:

TABLE 2

|  | Aniline | 2-ABP | 4-ABP |
| --- | --- | --- | --- |
| Starting Material | 1.45 mg/kg | 22.29 mg/kg | 6.77 mg/kg |
| Purified Material | 0.45 mg/kg | 0.57 mg/kg | <0.01 mg/kg |
| % Removed | 69 | 97 | >99 |

EXAMPLE 3 - CONTINUOUS PROCESS WITH ETHANOL

A solution of 12.5g technical DPA in 50ml ethanol (95%) was passed in the course of 1 hour at 20° C. over a column with a length of 72mm and an internal diameter of 10mm filled with 5.5g of the resin of Example 1. From the obtained eluate DPA was isolated by evaporation of the solvent. Obtained was 11.5g purified DPA (92% yield). Analysis by HPLC showed:

TABLE 3

|  | Aniline | 2-ABP | 4-ABP |
| --- | --- | --- | --- |
| Starting Material | 1.45 mg/kg | 22.29 mg/kg | 6.77 mg/kg |
| Purified Material | 0.11 mg/kg | 0.046 mg/kg | <0.01 mg/kg |
| % Removed | 92 | 99 | >99 |

EXAMPLE 4 - BATCH PROCESS WITH EMULSIFIABLE CONCENTRATE

Six 9000kg batches of emulsifiable concentrate were prepared from technical DPA having average impurity levels of about 40mg/kg of aniline, 7mg./kg of 4-ABP, and 18mg/kg of 2-ABP. The average concentrate contained about 31% (by weight) diphenylamine; a white mineral oil solvent; an emulsifier package consisting of a polyglycol ester, an ethoxylated fatty acid and an ethoxylated alkyl aryl phenol; and an antifoam. Each batch was prepared in a closed reactor provided with a stirrer and heated to 37–40° C. Resin as in Example 1 containing about 1.5% water (based on the weight of the batch) was then added, the mixture was stirred at about 37–40° C. for at least a 4-hour period, and the resin was separated. Analysis by HPLC of the purified batches gave average values (in mg/kg) of 0.039 aniline, <0.01 4-ABP, and 0.32 2-ABP.

What is claimed is:

1. A process for selectively removing primary amines from diphenylamine which comprises (a) bringing a solution containing said diphenylamine and an organic solvent into contact with a cationic exchange resin having a sulfonic acid group functionality in the presence of up to about 3 weight percent water, based on the weight of said solution, and (b) separating the resulting solution from said resin.

2. The process of claim 1 wherein the diphenylamine solution is continuously passed through a column of the cationic exchange resin.

3. The process of claim 1 wherein the solvent is acetone or ethanol.

* * * * *